United States Patent [19]

Jordan et al.

[11] Patent Number: 4,842,593

[45] Date of Patent: Jun. 27, 1989

[54] DISPOSABLE ABSORBENT ARTICLES FOR INCONTINENT INDIVIDUALS

[75] Inventors: William E. Jordan, Cincinnati; Leslie D. Ryan, Millville, both of Ohio

[73] Assignee: The Procter & Gamble Company, Cincinnati, Ohio

[21] Appl. No.: 107,226

[22] Filed: Oct. 9, 1987

[51] Int. Cl.$^4$ .................. A61F 13/16; A61F 13/18
[52] U.S. Cl. .................. 604/360; 604/367; 604/375
[58] Field of Search ............ 604/359, 360, 368, 358, 604/374, 375

[56] References Cited

U.S. PATENT DOCUMENTS

| | | | |
|---|---|---|---|
| 2,684,924 | 7/1953 | Rose et al. | 528/935 |
| 2,830,006 | 4/1958 | Birtwell et al. | 514/523 |
| 2,863,919 | 12/1958 | Birtwell et al. | 260/501.14 |
| 2,990,425 | 6/1961 | Senior | 524/195 |
| 3,067,745 | 12/1962 | Burgeni et al. | 128/285 |
| 3,533,725 | 10/1970 | Bridgeford | 428/375 |
| 3,658,790 | 4/1972 | Bernardin | 604/375 |
| 3,691,154 | 9/1972 | Bernardin | 604/375 |
| 3,691,271 | 9/1972 | Charle et al. | 424/28 |
| 3,707,148 | 12/1972 | Bryce | 128/284 |
| 3,794,034 | 2/1974 | Jones, Sr. | 128/290 R |
| 3,804,094 | 4/1974 | Manoussos et al. | 128/290 R |
| 3,843,701 | 10/1974 | Wortham | 260/448 R |
| 3,901,236 | 8/1975 | Assarsson et al. | 604/368 |
| 3,920,015 | 11/1975 | Wortham | 128/284 |
| 3,935,862 | 2/1976 | Kraskin | 128/287 |
| 3,964,486 | 6/1976 | Blaney | 128/284 |
| 4,059,114 | 11/1977 | Richards | 128/287 |
| 4,076,663 | 2/1978 | Masida et al. | 604/368 |
| 4,104,214 | 8/1978 | Meierhoefer | 604/368 |
| 4,200,735 | 4/1980 | Sano et al. | 536/30 |
| 4,286,082 | 8/1981 | Tsubakimoto et al. | 604/368 |
| 4,363,322 | 12/1982 | Andersson | 128/290 R |
| 4,372,309 | 2/1983 | Fowler | 128/284 |
| 4,583,980 | 4/1986 | Schneider et al. | 604/359 |
| 4,634,438 | 1/1987 | Sustmann et al. | 604/376 |
| 4,634,439 | 1/1987 | Sustmann et al. | 604/375 |
| 4,654,039 | 3/1987 | Brandt et al. | 604/368 |
| 4,657,537 | 4/1987 | Zimmerer | 604/360 |
| 4,661,101 | 4/1987 | Sustmann | 604/360 |
| 4,675,014 | 6/1987 | Sustmann et al. | 604/375 |
| 4,685,909 | 8/1987 | Berg et al. | 604/360 |

FOREIGN PATENT DOCUMENTS

| | | |
|---|---|---|
| 58-104276 | 6/1983 | Japan . |
| 61-209658A | 9/1986 | Japan . |
| 52-142559 | 6/1987 | Japan . |
| 2156370A | 10/1985 | United Kingdom . |

OTHER PUBLICATIONS

Nite Comfort Diaper Rash Buffer, undated product brochure Kaj Health Products, Inc., *Press Release*, "To Control & Prevent Diaper Rash", May 13, 1985.
The Newton Kansan, "Distribution Ready", Sep. 8, 1984, Nonwovens Industry, *Introducing the Tranquility System*, May, 1985.
Introducing the Tranquility System–undated product brochure.

*Primary Examiner*—C. Fred Rosenbaum
*Assistant Examiner*—Sharon Rose
*Attorney, Agent, or Firm*—George W. Allen; Jerry J. Yetter; Richard C. Witte

[57] ABSTRACT

Absorbent articles containing both an acidic buffering agent and a non-toxic, non-irritating, non-volatile antimicrobial agent are disclosed. The acidic buffering agent is preferably also an absorbent gelling agent which can imbibe aqueous body fluids in addition to acting as a buffer. Such articles are especially suitable for maintaining the pH of urine and feces discharged into the article at value below about 7.5. This in turn helps to prevent or reduce diaper rash and control odor caused by the production of ammonia.

15 Claims, 1 Drawing Sheet

DISPOSABLE ABSORBENT ARTICLES FOR INCONTINENT INDIVIDUALS

FIELD OF THE INVENTION

The present invention relates to disposable absorbent articles such as diapers, incontinence briefs and incontinence pads. Such articles comprise components which render them especially effective for absorbing discharged body fluids while at the same time preventing or reducing diaper rash and preventing or controlling odor.

BACKGROUND OF THE INVENTION

Diaper rash is a common form of irritation and inflammation of those parts of an infant's body normally covered by a diaper. This condition is also referred to as diaper dermatitis, napkin dermatitis, napkin rash, and nappy rash. While certainly more common in infants, this condition is not, in fact, limited to infants. Any individual who suffers from incontinence to the extent that the use of absorbent articles is required may develop this condition. This ranges from newborns, to the elderly, to critically ill or nonambulatory individuals.

It is generally accepted that true "diaper rash" or "diaper dermatitis" is a condition which is, in its most simple stages, a contact irritant dermatitis. The irritation of simple diaper rash results from extended contact of the skin with urine, or feces, or both. Diapers are worn to catch and hold the body waste, but generally hold the waste in direct contact with the skin until changed, i.e., in occluded fashion for long periods of time. The same is true for an incontinence pad, or incontinence brief. However, while it is known that the body waste "causes" diaper rash, the precise component or components of the urine or feces which are responsible for the resulting irritation of the skin have not been conclusively identified. The most commonly accepted list of factors linked to diaper rash includes ammonia, bacteria, the products of bacterial action, urine pH, *Candida albicans,* and moisture. These are generally cited in the art as being the most likely candidates for agents or conditions which produce or aggravate diaper rash.

As discussed in Berg and Stewart, U.S. Pat. No. 4,685,909, Issued Aug. 11, 1987, a primary cause of diaper rash appears to be a particular set of conditions which arises as a result of prolonged contact of skin with mixtures of feces and urine. Activity of proteolytic and lipolytic fecal enzymes, as well as fecal bacteria, present in such a mixture is believed to be a major factor in producing skin irritation. Urine in contact with enzymes and bacteria from feces can also result in production of ammonia which raises skin pH (and causes odor). This rise in skin pH, for example to levels of 6.0 and above, in turn increases that fecal proteolytic and lipolytic enzymatic activity which produces diaper rash. Urine itself can also contribute to diaper rash by adding moisture to the diaper environment. Water, and particularly water in the form of urine, is especially effective at diminishing the barrier property of skin, thereby enhancing the susceptibility of skin to fecal enzyme irritation. However, when skin pH is kept between about 3.0 and 5.5, the skin's barrier properties can be maintained. The foregoing diaper rash model suggests that effective diaper rash control can be achieved by maintaining skin pH well within the acidic range to inhibit irritation-producing enzymatic activity while simultaneously maintaining the diaper environment as dry as possible.

One factor in preventing a rise in skin pH to within the alkaline range involves the maintenance of aqueous fluids, e.g., urine, feces and/or mixtures thereof, discharged into and held within the diaper or incontinence article at an acidic pH. This can be accomplished by taking steps to inhibit ammonia formation in the article, by donating protons to the discharged liquids held within the absorbent article or by a combination of these methods. A number of prior art references, in fact, teach the addition of various acidic pH control or "ammonia-absorbing" agents to absorbent articles such as diapers, and agents of this type do tend to inhibit the rise of pH of aqueous fluids in the diaper. References with such disclosures include, for example, Alonso et al, U.S. Pat. No. 4,382,919, Issued May 10, 1983; Blaney, U.S. Pat. No. 3,964,486, Issued June 22, 1976; Bryce, U.S. Pat. No. 3,707,148, Issued Dec. 26, 1972; and Jones, Sr., U.S. Pat. No. 3,794,034, Issued Feb. 26, 1974.

One type of pH control agent or "buffering agent" frequently found in disposable absorbent articles comprises the slightly cross-linked polymeric gelling agents or "supersorbers" which serve to imbibe liquids discharged into the article. These materials frequently contain at least some unneutralized carboxylic acid or sulfonic acid groups in the polymer chain, and these acid groups can donate protons to fluid within the article. Polymeric gelling agents of this type are thus especially desirable components of the absorbent articles since they not only improve the absorbency characteristics of the article but they also provide at least some acid buffering capacity with respect to fluids in the article.

Whether the acidic pH control agent is of the polymeric gelling agent type or not, pH control agents alone will frequently not be able to provide sufficient buffering capacity to prevent a rise in the pH of urine or other discharged fluids within the absorbent article. This is because the amount of urine discharged into the typical absorbent article is often greater than the buffering capacity of the pH control agent can handle. Another factor which works against the action of an acidic buffering agent in inhibiting urine pH rise involves the presence of inorganic contaminants in the urine. Human urine, for example, frequently will contain bicarbonate salts which, after the urine is discharged, can decompose to produce $CO_2$. $CO_2$ dissipation from voided urine in turn tends to promote a rise in urine pH which can overcome whatever acid buffering capacity might be provided by the acidic pH control agent.

The foregoing considerations involving diaper rash, ammonia production and the importance of pH control of fluids within the absorbent article indicate that there is a continuing need to identify absorbent articles and components thereof which are especially effective for preventing the occurrence of conditions that favor the development of diaper rash and the production of odor-causing materials. Accordingly, it is an object of the present invention to provide disposable absorbent articles which are especially effective for reducing or preventing diaper rash and ammonia production. It is a further object of the invention herein to provide such absorbent articles which utilize readily available, non-toxic, non-irritating materials to provide the desired rash and odor combatting effectiveness. It is a further object of the present invention to provide absorbent articles of this type which can be prepared by relatively straightforward, conventional absorbent article production methods.

SUMMARY OF THE INVENTION

The present invention is directed to disposable absorbent articles useful for absorbing urine and feces discharged by incontinent individuals. Such articles also tend to reduce or prevent diaper rash and production of ammonia. Articles of this type essentially comprise a liquid impervious backsheet, a relatively hydrophobic liquid pervious topsheet and a flexible absorbent core positioned between the backsheet and the topsheet. The absorbent core itself comprises hydrophilic fiber material such as wood pulp fibers.

The essential component of the disposable absorbent articles herein which serves to combat diaper rash and odor is a pH control system. This pH control system consists essentially of an acidic buffering agent component and a non-toxic, non-irritating, non-volatile antimicrobial agent component. The buffering agent component and the antimicrobial agent component are present within the pH control system in a weight ratio of from about 3:1 to 2000:1.

The pH control system itself is present in the absorbent articles of the present invention in an amount which is effective to maintain the pH of *Proteus vulgaris*-contaminated, bicarbonate-containing urine discharged into the absorbent article at a value below about 7.5. Especially preferred buffering agents for use in the pH control system of these articles are the slightly cross-linked, partially neutralized polymeric gelling agents which function both as buffering agents and absorbents for aqueous liquids discharged into the absorbent article.

BRIEF DESCRIPTION OF THE DRAWING

The drawing submitted herewith represents a cutaway view of a disposable diaper which is a preferred configuration for the absorbent articles herein.

DETAILED DESCRIPTION OF THE INVENTION

The absorbent articles of the present invention can be manufactured in the configuration of wearable disposable absorbent products which are capable of absorbing significant quantities of aqueous body waste fluids such as urine and feces. Thus such articles, for example, may be prepared in the form of disposable diapers, adult incontinence briefs, adult incontinence pads and the like.

The absorbent articles herein will generally comprise at least three basic structural elements. One such element is a liquid impervious backing sheet. On top of this backing sheet is placed a second structural element which is an absorbent core. This absorbent core may itself comprise one or more distinct layers or zones. On top of this absorbent core is placed a third structural element which is a relatively hydrophobic, liquid pervious topsheet. The topsheet is the element of the article which is placed next to the skin of the wearer. In one embodiment, described more fully hereinafter, the articles herein will also include as a fourth structural element a flexible substrate, e.g., an insert, containing one or more components of the pH control system. Such an insert can be placed on top of the topsheet next to the skin of the wearer.

Especially preferred absorbent articles of this invention are disposable diapers. Articles in the form of disposable diapers are fully described in Duncan and Baker, U.S. Pat. No. Re. 26,151, Issued Jan. 31, 1967; Duncan, U.S. Pat. No. 3,592,194, Issued July 13, 1971; Duncan and Gellert, U.S. Pat. No. 3,489,148, Issued Jan. 13, 1970; and Buell, U.S. Pat. No. 3,860,003, Issued Jan. 14, 1975; which patents are incorporated herein by reference. A preferred disposable diaper for the purpose of this invention comprises an absorbent core; a topsheet superposed or co-extensive with one face of the core, and a liquid impervious backsheet superposed or co-extensive with the face of the core opposite the face covered by the topsheet. Both the backsheet and the topsheet most preferably have a width greater than that of the core thereby providing side marginal portions of the backsheet and topsheet which extend beyond the core. Frequently the backsheet and the topsheet will be fused together in these side marginal portions. The diaper is preferably constructed in an hourglass configuration.

The backsheet of the articles herein can be constructed, for example, from a thin, plastic film of polyethylene, polypropylene, or other flexible moisture impeding material which is substantially water impervious. Polyethylene, having an embossed caliper of approximately 1.5 mils, is especially preferred.

The topsheet of the article herein can be made in part or completely of synthetic fibers or films comprising such materials as polyester, polyolefin, rayon, or the like, or of natural fibers such as cotton. In nonwoven topsheets, the fibers are typically bound together by a thermal binding procedure or by a polymeric binder such as polyacrylate. This sheet is substantially porous and permits a fluid to readily pass therethrough into the underlying absorbent core.

Another suitable type of topsheet comprises the topsheets formed from liquid impervious polymeric material such as polyolefins. Such topsheets can have tapered capillaries of certain diameter and taper positioned in the topsheet to permit flow of discharged fluid through the topsheet into the underlying absorbent core of the article.

All of the topsheets used in the articles of the present invention are relatively hydrophobic in comparison with the absorbent core of said articles. Topsheet construction is generally disclosed in Davidson, U.S. Pat. No. 2,905,176, Issued Sept. 22, 1959; Del Guercio, U.S. Pat. No. 3,063,452, Issued Nov. 13, 1962; Holliday, U.S. Pat. No. 3,113,570, Issued Dec. 10, 1963, and Thompson, U.S. Pat. No. 3,929,135; Issued Dec. 30, 1975; which patents are incorporated herein by reference. Preferred topsheets are constructed from polyester, rayon, rayon/polyester blends, polyethylene or polypropylene.

The absorbent core, which may itself comprise one or more separate and/or distinct zones, e.g., layers, is positioned between the backing sheet and the topsheet to form the absorbent articles herein. Such an absorbent core essentially comprises a web or batt of hydrophilic fiber material. For purposes of the present invention, a fiber is "hydrophilic" if water or aqueous body fluid readily spreads on or over the surface of the fiber (without regard to whether or not the fiber actually imbibes fluid or forms a gel). The hydrophilic fibers which are employed in the absorbent core will generally have an average diameter which ranges from about 1 to 200 microns. More preferably, the average diameter of these hydrophilic fibers will range from about 10 to 100 microns. Substantially all of the hydrophilic fibers incorporated into the structures herein preferably have a fiber length of at least 1 mm.

The type of hydrophilic fiber material is not critical for use in the absorbent cores of the articles of the present invention. Any type of hydrophilic fiber which is suitable for use in conventional absorbent products is also suitable for use in the absorbent articles herein. Examples of hydrophilic fiber material include cellulose, modified cellulose, rayon, polyesters such as polyethylene terephthalate (DACRON), and the like. Suitable hydrophilic fibers also include hydrophobic fibers which have been hydrophilized with a hydrophilizing agent. Such fibers include surfactant-treated or silica-treated thermoplastic fibers derived, for example, from polyolefins such as polyethylene or polypropylene, polyacrylics, polyamides, polystyrenes, polyurethanes and the like.

For reasons of availability and cost, cellulosic fibers are generally preferred for use herein as the hydrophilic fiber component of the absorbent core. Most preferred are wood pulp fibers. However, other cellulosic fiber materials may also be used. Such other hydrophilic fiber materials include the stiffened, curled, cellulosic fibers which can be produced by cross-linking cellulose fibers with $C_{2-8}$ dialdehyde cross-linking agents. Fibers of this type can be defined in terms of their dry fiber and wet fiber twist counts (at least 4.5 twist nodes per millimeter dry and at least 3.0 twist nodes per millimeter wet) and by their fluid retention characteristics (average isopropyl alcohol retention value of less than 30%; average water retention value of from 28% to 50%). Stiffened, curled cellulosic fibers of this type are described in greater detail in European Patent Publication No. 252,650, published Jan. 13, 1988, in the name of the Buckeye Cellulose Corporation. This application, which corresponds to U.S. patent application Ser. No. 021,953, filed Mar. 5, 1987, is incorporated herein by reference.

Depending upon whether or not other materials are present in the absorbent core, hydrophilic fiber material will generally comprise from about 45% to 100% by weight of the absorbent core. Since components other than hydrophilic fiber will generally be present in the absorbent cores of the articles herein, hydrophilic fiber material will preferably comprise from about 60% to 95% by weight of the core, more preferably from about 70% to 90% by weight of the core.

The essential element of the absorbent articles herein which serves to combat diaper rash and odor comprises a pH control system. Such a pH control system may be either structural or nonstructural in character. This pH control system itself essentially comprises two components, i.e., an acidic buffering agent and a non-toxic, non-irritating, non-volatile antimicrobial agent. As described more fully hereinafter, such a pH control system serves to forestall the pH rise which would normally occur within discharged body fluids held within the disposable absorbent article. This effect in turn is believed to be responsible for preventing or minimizing the development of diaper rash and ammonia odor.

The acidic buffering agent component of the pH control system can be any one or more of a wide variety of non-toxic, non-irritating acidic materials which release protons when contacted with aqueous liquids. Thus these materials include low molecular weight organic or inorganic acids, high molecular weight polymeric acids or ion exchange resins and fibers in the hydrogen form.

Suitable low molecular weight organic and inorganic acid materials include such weak acids as citric acid, adipic acid, azelaic acid, malic acid, tartaric acid, gluconic acid, glutaric acid, levulinic acid, glycolic acid, succinic acid, fumaric acid, pimelic acid, suberic acid, sebacic acid and acid phosphate salts. These low molecular weight materials may be used in combination with their conjugate bases to provide buffer capacity.

High molecular weight polymeric acids which are useful as acidic buffering agents are those which are prepared from polymerizable, unsaturated, acid-containing monomers. Thus such monomers include the olefinically unsaturated acids and anhydrides which contain at least one carbon to carbon olefinic double bond. More specifically, these monomers can be selected from olefinically unsaturated carboxylic acids and acid anhydrides, olefinically unsaturated sulfonic acids and mixtures thereof. Examples of suitable high molecular weight polymeric acids prepared from such monomers include polyacrylic acid and its polyacrylate derivatives, poly(maleic acid) and its polymaleate derivatives, alginic acid, carboxymethylcellulose and the like. Polyacrylic acid and its polyacrylate derivatives useful as the acidic buffering agent component of the pH control system may be cross-linked or uncross-linked and may range in molecular weight from 1,000 to 5,000,000. Such acrylic acid-based materials include, for example, the Carbopol resins which are water-soluble polymers of acrylic acid cross-linked with such materials as polyallyl sucrose and polyallyl pentaerytritol. Such acrylic acid-based materials also include water-soluble polymers of acrylic acid cross-linked with such materials as polyallyl sucrose and polyallyl pentaerythritol. Such acrylic acid-based materials also include water swellable, cross-linked polyacrylates which can also serve, as hereinafter more fully described, as fluid absorbing agents.

Poly(maleic acid) and its polymaleate derivatives may also be used as acidic buffering agents in the pH control systems herein. Agents of this type may also be cross-linked or uncrosslinked and may range in molecular weight from 1,000 to 5,000,000. Poly(maleic acid) derivatives include poly(vinyl ether-maleic acid), and poly(methyl vinyl ether-maleic acid) such as the resins and poly(styrene-maleic acid) materials.

All of the foregoing higher molecular weight polymeric materials must be at least partially in the unneutralized, free acid form if they are to function as acidic buffering agents. Thus such materials will generally be no more than about 90% neutralized and preferably no more than about 80% neutralized.

Another useful type of acidic buffering agent for use in the pH control system of the instant articles comprises ion exchanging, proton-donating modified cellulose materials in fiber form. This includes, for example, carboxymethylcellulose in the free acid form, oxidized cellulose, sulfoethyl cellulose and phosphorylated cellulose ("cellulose phosphate") prepared by conventional techniques. Phosphorylated cellulose, for example, can be prepared by treating cellulose with solutions of urea and phosphoric acid, with phosphorus oxychloride and pyridine, with phosphorus oxychloride and phosphoric acid, with phosphorus oxychloride and dioxane or with phosphorus oxychloride alone. Examples of methods for preparing phosphorylated cellulose ion-exchanging fibers are described in Bernardin, U.S. Pat. No. 3,691,154, Issued Sept. 12, 1972, and Bernardin, U.S. Pat. No. 3,658,790, Issued Apr. 25, 1972. Methods for preparing other types of ion-exchanging cellulose derivatives are described in Sano et al, U.S. Pat. No. 4,200,735, Issued Apr. 29, 1980, Ward et al, U.S. Pat. No. 3,854,868, Issued Dec. 17, 1974 and Bridgeford, U.S. Pat. No. 3,533,725, Issued Oct. 13, 1970. All of the foregoing patents are incorporated herein by reference.

Modified cellulose ion-exchanging fibers for use in their hydrogen form as acidic buffering agents in the pH control system of the present invention preferably have an ion-exchange capacity of at least about 0.4 meq./gram, more preferably at least about 1.0 meq./gram. Cellulose-derived acidic buffering agents are especially advantageous for incorporation into the absorbent core of the articles herein since such acidic ion-exchanging fibers can easily be admixed with the hydrophilic fibers essentially present in the absorbent core.

One highly preferred type of acidic buffering agent comprises the hydrogel-forming, polyacid-based absorbent gelling agents. These gelling agents, in addition to acting as buffering agents, also act as absorbents or gellants for aqueous fluids discharged into the absorbent core. Hydrogel-forming polymeric buffering agents of this type are those which, upon contact with fluids (i.e., liquids) such as water or body fluids, imbibe such fluids and thereby form hydrogels. In this manner, fluid discharged into the absorbent structures herein can be acquired and held by such absorbent gelling agent buffers. These preferred absorbent gelling agent buffers used herein will generally comprise substantially water-insoluble, slightly cross-linked, partially neutralized, hydrogel-forming polymer materials prepared from polymerizable, unsaturated, acid-containing monomers. In such materials, the polymeric component formed from unsaturated, acid-containing monomers may comprise the entire gelling agent or may be grafted on to other types of polymer moieties such as starch or cellulose. Acrylic acid grafted starch materials are of this latter type and are especially preferred for use herein. Thus the preferred absorbent gelling agent buffers include hydrolyzed acrylonitrile grafted starch, acrylic acid grafted starch, polyacrylates, maleic anhydride-based copolymers and combinations thereof. Especially preferred absorbent gelling buffers are the polyacrylates and acrylic acid grafted starch.

Whatever the nature of the basic polymer components of the preferred hydrogel-forming absorbent buffering agents, such materials will in general be slightly cross-linked. Cross-linking serves to render these preferred hydrogel-forming absorbent buffering agents substantially water-insoluble, and cross-linking also in part determines the gel volume and extractable polymer characteristics of the hydrogels formed therefrom. Suitable cross-linking agents are well known in the art and include, for example, (1) compounds having at least two polymerizable double bonds; (2) compounds having at least one polymerizable double bond and at least one functional group reactive with the acid-containing monomer material; (3) compounds having at least two functional groups reactive with the acid-containing monomer material; and (4) polyvalent metal compounds which can form ionic cross-linkages. Cross-linking agents of the foregoing types are described in greater detail in Masuda et al; U.S. Pat. No. 4,076,663; Issued Feb. 28, 1978, incorporated herein by reference. Preferred cross-linking agents are the di-or polyesters of unsaturated mono-or polycarboxylic acids with polyols, the bisacrylamides and the di-or triallyl amines. Especially preferred cross-linking agents are N,N'-methylenebisacrylamide, trimethylol propane triacrylate and triallyl amine. The cross-linking agent will generally comprise from about 0.001 mole percent to 5 mole percent of the preferred hydrogel-forming polymeric gelling agent buffer materials. More preferably, the cross-linking agent will comprise from about 0.01 mole percent to 3 mole percent of the absorbent buffering agents used herein.

The preferred slightly cross-linked, hydrogel-forming absorbent buffering agents will generally be employed in their partially neutralized form. For purposes of this invention, such materials are considered partially neutralized when at least 25 mole percent, and preferably at least 50 mole percent of monomers used to form the polymer are acid group-containing monomers which have been neutralized with a salt-forming cation. Suitable salt-forming cations include alkali metal, ammonium, substituted ammonium and amines. This percentage of the total monomers utilized which are neutralized acid group-containing monomers is referred to herein as the "degree of neutralization." As indicated hereinbefore, such materials must not have a degree of neutralization greater than about 90% if they are to be useful as acidic buffering agents in the articles herein.

The preferred absorbent gelling agent buffers used in the pH control system of the articles herein are those which have a relatively high capacity for imbibing fluids encountered in the absorbent articles. This capacity can be quantified by referencing the "gel volume" of the absorbent gelling agent buffers which are preferably used in the present invention. For purposes of this invention, gel volume can be defined in terms of the amount of synthetic urine absorbed by any given absorbent gelling agent buffer and is specified as grams of synthetic urine per gram of gelling agent.

Gel volume in synthetic urine can be determined by forming a suspension of about 0.1–0.2 parts of dried absorbent gelling agent buffer to be tested with about 20 parts of this synthetic urine. This suspension is maintained at ambient temperature under gentle stirring for about 1 hour so that swelling equilibrium is attained. Using a procedure described in greater detail hereinafter in the Test Methods section, the gel volume of the absorbent gelling agent buffer in grams of synthetic urine per gram of absorbent gelling agent buffer is then calculated from the weight fraction of the gelling agent in the suspension and the ratio of the liquid volume excluded from the formed hydrogel to the total volume of the suspension. The preferred absorbent gelling agent buffers useful in this invention will have a gel volume of from about 20 to 70 grams, more preferably from about 30 to 60 grams, of synthetic urine per gram of absorbent gelling agent buffer.

Another feature of the preferred absorbent gelling agent buffers which are useful as one component of the pH control system of the articles herein relates to the level of extractable polymer material present in such hydrogel-forming buffers. Extractable polymer levels can be determined by contacting a sample of preferred hydrogel-forming absorbent gelling agent buffer material with a synthetic urine solution for the substantial period of time (e.g., at least 16 hours) which is needed to reach extraction equilibrium, by then filtering the formed hydrogel from the supernatant liquid, and finally by then determining the polymer content of the filtrate. The particular procedure used to determine extractable polymer content of the preferred absorbent gelling agent buffers herein is set forth in Brandt, Goldman and Inglin; U.S. Pat. No. 4,654,039; Issued Mar. 1, 1987, incorporated herein by reference. The absorbent gelling agent buffer materials which are especially useful in the absorbent articles herein are those which have an equilibrium extractables content in synthetic urine of no more than about 17%, preferably no more than about 10% by weight of the absorbent gelling agent buffer.

The absorbent gelling agent buffers hereinbefore described can be incorporated into the cores of the absorbent articles of the present invention in the form of discrete particles. Such absorbent gelling agent buffer particles can be of any desired shape, e.g., spherical or semi-spherical, cubic, rod-like polyhedral, etc. Shapes having a large greatest dimension/smallest dimension ratio, like needles and flakes are also contemplated for use herein. Agglomerates of absorbent gelling agent buffer particles may also be used.

The size of the absorbent gelling agent buffer particles may vary over a wide range. For reasons of industrial hygiene, average particle sizes smaller than about 30 microns are less desirable. Particles having a smallest dimension larger than about 2 mm may also cause a feeling of grittiness in the absorbent article, which is undesirable from a consumer aesthetics standpoint. Furthermore, rate of fluid absorption can be affected by particle size. Larger particles have very much reduced rates of absorption. Preferred for use herein are absorbent gelling agent buffer particles substantially all of which have a particle size of from about 30 microns to about 2 mm. "Particle Size" as used herein means the weighted average of the smallest dimension of the individual particles.

The amount of polymeric gelling agent buffer particles articles herein will depend upon the degree of buffering and absorbent capacity desired and the nature of the antimicrobial agent in the pH control system as discussed more fully hereinafter. If, however, the absorbent gelling agent buffer is to effectively function as an absorbent or well as a buffer, the absorbent gelling agent buffer particles must be present in the absorbent core in particular concentrations. Thus, absorbent gelling agent buffers will preferably comprise from about 2% to 50% by weight of the absorbent core, more preferably from about 5% to 20% by weight of the absorbent core.

When absorbent gelling agent buffer particles are to be used in the hydrophilic fiber-containing cores of the absorbent articles herein, such cores can be prepared by any process or technique which provides a web comprising a combination of the fibers and the gelling agent buffer particles. For example, web cores can be formed by air-laying a substantially dry mixture of hydrophilic fibers and absorbent gelling agent buffer particles and, if desired or necessary, by densifying the resulting web. Such a procedure is described more fully in Weisman and Goldman; U.S. Pat. No. 4,610,678; Issued Sept. 9, 1986, incorporated herein by reference. As indicated in this U.S. Pat. No. 4,610,678, the air-laid webs formed by such a procedure will preferably comprise substantially unbonded fibers and will preferably have a moisture content of 10% or less.

The density of the absorbent cores which comprise webs of hydrophilic fibers and absorbent gelling agent buffer particles can be of some importance in determining the absorbent properties of the cores and of the absorbent articles in which such cores are employed. The density of such absorbent cores herein will preferably be in the range of from about 0.06 to about 0.3 $g/cm^3$, and more preferably within the range of from about 0.09 to about 0.22 $g/cm^3$. Typically the basis weight of the absorbent cores herein can range from about 0.02 to 0.12 $g/cm^2$.

Density values for cores of this type are calculated from basis weight and caliper. Caliper is measured under a confining pressure of 0.137 psi (0.94 kPa). Density and basis weight values include the weight of the hydrogel-forming buffer particles. Density of the cores herein need not be uniform throughout the core. Within the density ranges hereinbefore set forth, the cores can contain regions or zones of relatively higher or relatively lower density.

The second essential component of the pH control system utilized in the absorbent articles herein is an antimicrobial agent. An antimicrobial agent, for purposes of this invention, can be any substance or moiety which either destroys microorganisms (e.g., bacteria) or inhibits, suppresses or prevents their growth and/or metabolism when such microorganisms are present in the articles herein. The antimicrobial agents useful in the absorbent articles of the present invention are substances of this type which are also substantially non-toxic, nonirritating and non-volatile as more particularly hereinafter defined.

It is believed that the antimicrobial agent functions in the pH control systems herein by preventing or reducing microbial growth or metabolism in the discharged liquid held within the absorbent articles herein. Such reduced microbial growth or metabolism prevents or reduces microbial action on discharged urine and/or feces in the article to thereby prevent or minimize ammonia production. This is important since excessive ammonia production, especially in the presence of bicarbonate-containing urine, will cause a rise in skin pH in the diaper/brief area, even in the presence of a buffering agent. The antimicrobial agent component of the pH control system thus works in combination with the acidic buffering agent to maintain the pH of discharged fluid in the absorbent article below about 7.5. This, in turn, facilitates the maintenance of an acidic skin pH in the diaper/brief area. Since ammonia production is minimized, odor problems associated with the presence of ammonia can also be alleviated.

Antimicrobial agents including those useful in the pH control system herein are generally well known materials. For example, an extensive disclosure of various types of antimicrobial agents is found in Kirk-Othmer; *Encyclopedia of Chemical Technology, Third Edition, Vol. 7*, (1979) pp 793–832, and this publication is incorporated herein by reference. Of all the antimicrobial agents disclosed in this reference, those which are substantially non-toxic, non-irritating and non-volatile are suitable for use in the pH control system of the present invention.

Since absorbent articles containing the pH control system components are to be maintained in contact with the wearer's skin, the antimicrobial agent component of the pH control system, like the acidic buffer, must be one which is substantially non-toxic and non-irritating. An antimicrobial agent is substantially non-toxic and non-irritating if, during the period the absorbent articles are worn, the antimicrobial agent by virtue of its chemical and physical characteristics causes substantially no toxic substance to be released into the body of the wearer and no significant amount of irritation or reddening of the wearer's skin.

Antimicrobial agents used in the pH control system of the absorbent articles herein must also be substantially non-volatile. Non-volatile antimicrobial agents are those which will not evaporate or sublime out of the absorbent article to any significant degree during the time period between manufacture and use of the article. Thus, antimicrobial agents in solid form or antimicrobial agents which leave solid residues are preferred for incorporation into the absorbent articles herein. On the other hand, antimicrobial agents in liquid form, such as alcoholic antimicrobials, should not be utilized.

Of the various types of antimicrobial agents known in the art, highly preferred for use herein are the quaternary nitrogen-based antimicrobials and the bis-biguanides. These two types of antimicrobial agents have a combination of desirable properties (e.g., relatively high antimicrobial activity, relatively low toxicity and irritation potential and acceptable physical characteristics) which make them especially suitable for use in the articles of this invention.

The antimicrobial agents which contain a single quaternary nitrogen moiety include the hydrocarbyl substituted ammonium compounds as well as those compounds wherein the quaternary nitrogen is part of a heterocyclic ring, e.g., pyridinium compounds. Representative examples of suitable quaternary nitrogen-based antimicrobial agents include methylbenzethonium chloride, benzalkonium chloride, dodecyltrimethyl ammonium bromide, tetradecyltrimethyl ammonium bromide and hexadecyltrimethyl ammonium bromide. Heterocyclic quaternary nitrogen-based antimicrobial agents include dodecylpyridinium chloride, tetradecylpyridinium chloride, cetylpyridinium chloride (CPC), tetradecyl-4-ethylpyridinium chloride and tetradecyl-4-methylpyridinium chloride.

Other preferred antimicrobial agents are the bis-biguanides. The bis-biguanides are also known antimicrobial agents. They are described in detail, for example, in Rose et al, U.S. Pat. No. 2,684,924, Issued July 27, 1954; Senior et al, U.S. Pat. No. 2,990,425, Issued June 27, 1961; Birtwell et al, U.S. Pat. No. 2,830,006, Issued Apr. 8, 1958; and Birtwell et al, U.S. Pat. No. 2,863,919, Issued Dec. 9, 1958, which patents are incorporated herein by reference. The most preferred bis-biguanides are 1,6-bis(4-chlorophenyl)diguanidohexane, known as chlorhexidine, and its water-soluble salts. Especially preferred are the hydrochloride, acetate and gluconate salts of chlorhexidine.

Several other types of antimicrobial agents may also be especially useful in the articles herein. These include the carbanilides, substituted phenols, metal compounds and rare earth salts of surfactants. Carbanilide materials include 3,4,4'-trichlorocarbanilide (TCC, triclocarban) and 3-(trifluoromethyl)-4,4'-dichlorocarbanilide (IRGASAN). Substituted phenols include 5-chloro-2-(2,4-dichlorophenoxy)phenol (IRGASAN DP-300). Metal compounds include zinc and stannous salts such as zinc chloride, zinc sulfate and stannous chloride. Rare earth salts of surfactants are disclosed in European Patent Application No. EP-A-10819; Published Oct. 29, 1980, which application is incorporated herein by reference. Rare earth salts of this type include the lanthanum salts of linear $C_{10}$–$C_{18}$ alkylbenzene sulfonates (LaLAS).

Some antimicrobial agents useful herein may be acidic in form and thus, it is possible that such agents could function as the acid buffer in the pH control systems herein in addition to acting as antimicrobial agents. It is preferred, however, that the acidic buffering agent and antimicrobial agent components of the pH control system not be the same material or moiety. Rather the acidic buffering agent and antimicrobial agent are preferably separate and distinct species, e.g., separate and distinct elements, compounds or moieties. Whatever the nature of the antimicrobial agent component, it will generally be present in the pH control system of the absorbent articles herein in an amount such that the weight ratio of acidic buffering agent to antimicrobial agent ranges from about 3:1 to 2000:1. More preferably, the weight ratio of buffering agent to antimicrobial agent within the pH control system will range from about 25:1 to 1000:1. As can be seen from these ratios, the amounts of buffering agent and antimicrobial agent relative to each other can vary widely. This is because of the broad range of antimicrobial activity encountered in the various types of antimicrobial agents which can be used in the pH control systems herein.

The overall concentration of the pH control system in the absorbent articles of the present invention will depend upon the relative buffering capacity of the particular buffering agent selected and the relative strength of the particular antimicrobial agent employed. However, an appropriate concentration of the pH control system can be determined by referencing the effectiveness of the system in combatting the ammonia-producing effects of one particular microorganism, *Proteus vulgaris*. *Proteus vulgaris* is a microorganism which is representative of species which are commonly found in the intestinal tract and which are capable of degrading urea in urine to ammonia. Furthermore, *Proteus vulgaris* is a microorganism which is relatively resistant to antimicrobial agents and which is thus in general relatively difficult to control using antimicrobial agents.

The two-component pH control system should be utilized in the articles herein in an amount which is effective to maintain the pH of *Proteus vulgaris*-contaminated, bicarbonate-containing urine discharged into the article at a value below about 7.5. More preferably, the pH control system should maintain the pH of *Proteus vulgaris*-contaminated, bicarbonate-containing urine discharged into the article at a value below about 6.5. A standard procedure for determining the effectiveness of the pH control system in maintaining pH within these limits is set forth hereinafter in the examples.

When the acidic buffering agent is a partially neutralized, slightly cross-linked, hydrogel-forming absorbent gelling agent as hereinbefore described in detail, and when the antibacterial agent is selected from quaternary nitrogen-based compounds and bis-biguanides, and when the pH control system is found entirely within the absorbent core of the article, it is generally possible to specify the concentration of the pH control system by quantifying the amount of absorbent gelling agent buffer and the amount of the antimicrobial agent in the core. Thus preferably pH control systems of this type are utilized in an amount such that the absorbent gelling agent buffer comprises from about 2% to 50% by weight of the core and the antimicrobial agent comprises from about 0.02% to 2.0% by weight of the core. More preferably in articles of this type, the absorbent gelling agent buffer will comprise from about 5% to 20% by weight of the absorbent core, and the antimicrobial agent will comprise from about 0.05% to 1.0% by weight of the core.

The two components of the pH control system incorporated into the absorbent articles herein may or may not comprise distinct, discernible structural elements of the articles. Thus, for example, either buffering agent and/or antimicrobial agent may be utilized in discrete particulate (including fiber) form such that these components are readily discernible within the article. Alternatively, one or both of the pH control system components may be intimately associated, for example, by coating, by impregnating, or by actually chemically bonding, with one of the other structural elements (e.g., the topsheet, the absorbent core or an insert layer) of the article.

In one embodiment of the articles herein, the acidic buffering agent component of the pH control system is a partially neutralized, slightly cross-linked hydrogel-forming polycarboxylate absorbent gelling agent in particulate form and, as hereinbefore described, is incorporated into the absorbent core of the absorbent articles by intimately admixing such gelling agent particles with the hydrophilic fiber material which forms the core.

In another embodiment of the articles here, the antimicrobial agent component of the pH control system is impregnated into the hydrophilic fiber material forming the absorbent core. This can be accomplished either before or after the absorbent core is formed. In embodiments wherein the absorbent core is formed by airlaying the hydrophilic fibers to form a web, for example, in the manner described in the hereinbefore referenced U.S. Pat. No. 4,610,678, the antimicrobial agent can actually be incorporated, e.g., impregnated, into the drylap used to form the hydrophilic fibers.

In yet another embodiment, the pH control system or components thereof may be incorporated on or in a water-insoluble, flexible substrate which is positioned on top of the topsheet of the absorbent article next to the wearer's skin. This substrate may be provided as an insert or liner which may or may not be affixed to the article topsheet. The water-insoluble flexible substrate used to deliver pH control system components in this insert or liner embodiment can comprise any suitable material which will act as a carrier for such components. Thus the substrate can be in the form of cloth, a nonwoven substrate, e.g., paper, a film, or a sponge structure. Such substrates can be constructed of, for example, cellulose fiber, polyolefins, polyesters, rayon, and the like.

The pH control system component or components can be combined with the flexible insert or liner substrate in any manner which provides the component(s) in releasable form. Thus pH control system component(s), in either solid or liquid form, can be admixed with the substrate material as the substrate is being formed. Alternatively, the component(s) can be added to, impregnated in or sprayed on the insert or liner substrate after the substrate is formed.

The insert or liner substrate will generally not be large enough to cover the entire area of the article topsheet. Preferably the insert or liner will cover only from about 20% to 90% of the top surface area of the topsheet on which the insert substrate is placed. Thickness of the insert or liner substrate can vary widely depending upon the substrate type and the amount and type of pH control system component(s) it carries. Insert or liner substrates useful herein will generally range in thickness from about 0.2 to 1.5 cm.

The insert or liner substrate can be actually secured to the topsheet of the absorbent article in order to ensure that the insert or liner is properly positioned once the absorbent article is applied to the wearer. Thus the insert or liner may be glued to the topsheet or otherwise affixed using two-sided adhesive tape or similar attaching means. Alternatively the insert or liner substrate may simply be positioned on the absorbent article topsheet at the time the article is applied and not affixed to the topsheet in any way.

Figure 1:
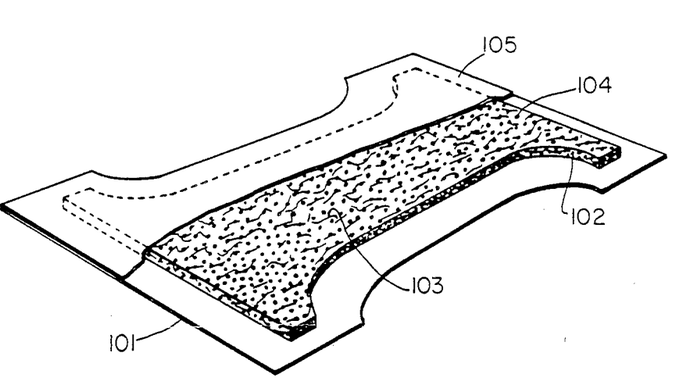

An embodiment of the disposable absorbent articles herein in the form of a disposable diaper is shown in the drawing. The hourglass-shaped diaper structure of the drawing comprises a liquid impervious backing sheet 101. Positioned on the top of the backing sheet 101 is an hourglass-shaped absorbent core 102 containing the pH control system of the present invention. This core contains hydrophilic fiber material 103 such as wood pulp fiber, impregnated with an antimicrobial agent such as cetylpyridinium chloride. Also distributed throughout the absorbent core 102 are particles 104 of absorbent gelling agent buffer. These particles serve both as a buffering agent and as a gelling agent which imbibes fluid reaching the diaper core. Positioned on top of the hourglass-shaped absorbent core 120 is liquid pervious topsheet 105.

TEST METHODS

In describing the preferred embodiments of the present invention, characteristics of absorbent gelling agent buffer particles are specified. Where reported, these gel volume characteristics can be determined using the following test method:

Gel volume in terms of grams of synthetic urine absorbed per gram of absorbent gelling agent buffer is determined by swelling the polymer samples in several aliquots of synthetic urine. The amount of such synthetic urine actually absorbed by the absorbent gelling agent buffer is determined by a procedure which involves use of a synthetic urine solution containing Blue Dextran so that optical absorbance measurements can be used to calculate the amount of synthetic urine that is not taken up by the hydrogel which forms.

(a) Blue Dextran Solution Preparation

A 0.03% Blue Dextran (BD) solution is prepared by dissolving 0.3 parts of Blue Dextran (Sigma D-5751) in 1000 parts of Synthetic Urine (SU) solution. Synthetic Urine is 15.0 parts of 1% TRITON X-100, 60.0 parts of NaCl, 1.8 parts of $CaCl_2.2H_2O$, and 3.6 parts of $MgCl_2.6H_2O$, diluted to 6000 parts with distilled $H_2O$. The resulting solution has an absorbance of about 0.25 at its absorbance maximum of 617 nm.

(b) Hydrogel Equilibration

Aliquots of the hydrogel-forming absorbent gelling agent buffer to be tested are swelled in (i) 20 parts of Synthetic Urine (SU) solution and (ii) 20 parts of Blue Dextran (BD) solution. The suspension in the Blue Dextran (BD) solution is prepared in duplicate. For most hydrogels, 0.1–0.25 parts of hydrogel-forming dried powder is required to give a sufficiently high spectrophotometer reading relative to the Blue Dextran reference solution. One hour of equilibration at ambient temperature under gentle stir-bar stirring is usually sufficient for swelling equilibrium to be attained. After equilibration, a 3 ml aliquot of supernatant is separated from each gel suspension by decantation followed by centrifugation.

(c) Gel Volume Determination

The optical absorbency (ABS) of each supernatant is determined spectrophotometrically with an accuracy of 0.001 absorbance units. The Synthetic Urine solution is used as an ABS=0.0 reference. The absorbency of the supernatant from the synthetic urine suspension without Blue Dextran should not exceed 0.01 A; higher values indicate scattering from residual hydrogel gel particles or residual additives, and further centrifugation is necessary. The absorbency of the Blue Dextran supernatants should exceed the absorbency of the Blue Dextran reference solution by at least 0.1 absorbance units. Absorbency values below this range indicate the need to adjust the amount of polymeric gelling agent used to prepare the gel suspension.

(d) Gel Volume Calculation

The Gel Volume in synthetic urine of the absorbent gelling agent buffer in gms/gm is calculated from (i) the weight fraction of the absorbent gelling agent buffer in the gel suspension and (ii) the ratio of the excluded volume to the total volume of the suspension. Since Blue Dextran is excluded from the hydrogel due to its high molecular weight, this ratio is related to the measured absorbencies. The following equation is used to calculate the gel volume:

$$\text{Gel Volume} = \left[ \frac{(\text{gms } BD \text{ Solution})}{(\text{gms absorbent gelling agent}^*)} \right] \times$$

$$\left[ 1 - \frac{(ABS\ BD \text{ solution})}{(ABS\ BD \text{ supernatant} - ABS\ SU \text{ supernatant})} \right]$$

*Corrected to a dry weight basis

The various embodiments of the absorbent articles hereinbefore described are illustrated by the following examples:

EXAMPLE I An adult incontinence product is prepared with an air-laid absorbent core of southern softwood/pine fibers (Foley fluff) having distributed therein buffer particles of partially neutralized, sodium polyacrylate gelling agent buffer and having impregnated therein cetylpyridinimm chloride (CPC) antimicrobial agent. This air-laid core is prepared by disintegrating CPC-impregnated drylap and airlaying the resulting fibers into an absorbent web.

A. Drylap Preparation

To impregnate the drylap, a standard roll of Foley drylap, cut to the desired wight, is placed in a cylindrical tank containing a mixture of CPC and ethyl alcohol (15.3 mg of CPC per ml of EtOH). The CPC/EtOH solution is allowed to wick into the drylap completely. The soaked drylap is then placed in an oven equipped with an air blower. The air blower is run (no oven heat) until all of the alcohol is evaporated. Target concentration of CPC in the drylap is 10 mg of CPC per gram of drylap (1% by weight).

B. Absorbent Core Preparation

Two separate layers of fibrous webs are used to form the absorbent core of the adult incontinence product of this example. A primary, generally hourglass-shaped layer containing little or no gelling agent is used as an overlay to a smaller generally rectangular insert layer containing approximately 30% by weight of the insert of absorbent gelling agent buffer particles. Both the overlay and the insert are made from the CPC-impregnated drylap hereinbefore described.

For both layers, the CPC-impregnated drylap is fed into a millhouse disintegrator for disintegration and fluffing. For the overlay layer, this fluffed material is air-conveyed through a disperser where it is further fluffed and dispersed prior to laydown on a 40×40 copper wire screen. For the insert layer, 70% neutralized sodium polyacrylate gelling agent buffer particles (gel volume =40 g/g) are dispersed into an air stream and laid down simultaneously with the fluff drylap on the copper screen in the manner generally described in the hereinbefore referenced U.S. Pat. No. 4,610,678.

Both the overlay and the gelling agent-containing insert webs are conducted to a calender roll where they are compressed to the desired density (0.048 g/cm$^3$ for the overlay; 0.047 g/cm$^3$ for the insert). The basis weight target for the overlay is 0.031 g/cm$^2$ (0.20 g/in$^2$). The target basis weight for the insert is 0.026 g/cm$^2$ (0.17 g/in$^2$).

C. Article Preparation

The two types of webs hereinbefore described are fashioned into a multi-layer adult incontinence product. Such a product comprises a formed film topsheet prepared from polyethylene with a plurality of tapered capillaries in the general manner described in the hereinbefore-referenced U.S. Pat. No. 3,929,135. The hourglass-shaped primary absorbent layer is positioned beneath the topsheet and the rectangular insert layer is positioned beneath the primary absorbent layer in a manner such that the insert is generally positioned toward the front of the incontinence product. A fluid impervious polyethylene backing sheet is positioned underneath the two airfelt layers which form the absorbent core.

Both the topsheet and the backsheet have a width substantially greater than that of the absorbent core, and the topsheet and backsheet are fused to each other in the side marginal portions of these elements which extend beyond the core. Elastic material is positioned within these extended fused side marginal portions in the manner described in Buell; U.S. Pat. No. 3,860,003; Issued Jan. 14, 1975.

Such an incontinence product, which contains both CPC and an absorbent gelling agent buffer within the absorbent core, is especially effective at maintaining the pH of *Proteus vulgaris*-contaminated urine discharged into the device at a value below about 7.5.

EXAMPLE II

CPC-containing drylap, prepared in the manner described in Example I, is also used to prepare cores for disposable diaper products. As with the adult incontinence product of Example I, the diapers herein also have a dual layer absorbent core. These cores are made in the same general manner set forth in Example I for the incontinence product cores.

The primary layer of the absorbent core is an hourglass-shaped web of CPC-impregnated Foley fluff containing about 15% by weight of the same 70% neutralized sodium polyacrylate gelling agent buffer used in Example I. The hourglass-shaped layer has a basis weight of approximately 0.0315 g/cm$^2$ (0.203 g/in$^2$).

The insert layer of the absorbent core also comprises CPC-impregnated Foley fluff containing about 15% by weight of the gelling agent buffer particles. The insert has a basis weight of approximately 0.039 g/cm$^2$ (0.252 g/in$^2$).

A dual core disposable diaper is prepared utilizing a thermally bonded polypropylene topsheet, the hourglass-shaped primary core hereinbefore described positioned below the topsheet, the oval insert hereinbefore described positioned underneath the hourglass-shaped core and a fluid-impervious polyethylene backing sheet underneath the hourglass and insert core layers. The oval insert is positioned toward the front half of the diaper such that the front one-third section of the diaper core has a higher basis weight than does the back two-thirds of the diaper core. Such a CPC and gelling agent-containing diaper is especially effective at maintaining pH of *Proteus vulgaris*-contaminated urine discharged into the diaper at a value below about 7.5.

EXAMPLE III

A model has been developed to test the ability of Foley fluff absorbent cores containing various types of pH control systems to maintain *Proteus vulgaris*-contaminated urine within the alkaline range over a 24-hour period. The materials and test methods used in such a model are described as follows:

Bicarbonate-Rich Urine

Urine samples from two human donors are passed through a sterilizing filter (Nalgene, 0.45μ pore). The pH is then adjusted to 6.2 (if necessary 1N HCl or 1N NaOH), and nitrogen gas bubbled into the urine for 30 minutes (room temperature). The pH is measured again and adjusted to 6.2 if necessary. Bubbling of nitrogen gas through the urine sample is repeated and pH is readjusted to 6.2 until the pH virtually stabilizes (i.e., pH 6.15–6.25). Usually three nitrogen bubblings are sufficient. This pH 6.2 bicarbonate-depleted urine is passed through a sterilizing filter again. Then 1.5 mg of sodium bicarbonate is added per ml of urine. The pH is adjusted to 6.8 (if necessary). These bicarbonate-rich urine samples are used immediately, with care taken to minimize $CO_2$ loss (minimum headspace, 4° C. temperature).

Fluff-Containing Antimicrobials

Foley drylap is treated with either an aqueous or ethanolic solution of the antimicrobial agent to be tested. After drying (18 hours, room temperature in a hood), the drylap is converted to fluff (airfelt) in a Waring blender and stored in a plastic container until used. Test swatches weighing 1 gram are prepared from this airfelt by forming the airfelt into a cohesive patch. Some test swatches contain about 15% by weight of particles of a 70% neutralized sodium polyacrylic gelling agent (gel volume=40 g/g) which serves as an acidic buffering agent.

*Proteus vulgaris* Inoculum

The ammoniogenic bacterium *Proteus vulgaris* is grown in trypticase soy broth (TSB) medium containing no dextrose. Cloudy suspensions of *Proteus vulgaris* (18-hour cultures) are measured for optical density at 420nm. If necessary, these bacterial suspensions are diluted with TSB to obtain an optical density between 1.0 and 1.7, and are then used as the bacterial inoculum (1:100) in the testing.

Testing System

A test swatch of desired fluff is placed in an 8 oz. wide mouth glass jar. Bicarbonate-rich urine of an initial measured pH of about 6.8 and containing 1 ml of *Proteus vulgaris* suspension per 100 ml is added to the test swatch (4X loading), then tamped down with a glass piston to a uniform wad. The jar lid is secured, followed by a 24-hour incubation at 37° C. The pH (24-hour) is then measured using a surface electrode and recorded. These initial and 24-hour pH values are tabulated for each system and are set forth in Table I.

TABLE I

Effect of Antimicrobial Agents and Polymeric Gelling Agent (PGA) Buffers on pH of *Proteus Vulgaris*-Contaminated, Bicarbonate-Containing Urine

| Antimicrobial Agent | Antimicrobial Concentration (mg/gm fluff) | 100% Fluff pH 0 Hr. | 100% Fluff pH 24 Hrs. | 85% Fluff 15% PGA pH 0 Hr. | 85% Fluff 15% PGA pH 24 Hrs. |
|---|---|---|---|---|---|
| Fluff Control | (No *Prot. Vulg.*) | 6.80 | 8.04 | 6.85 | 6.27 |
| Fluff Control | (*Prot. Vulg.* Innoc.) | 6.80 | 9.31 | 6.85 | 8.90 |
| Chlorhexidine | 2.0 | 6.80 | 7.61 | 6.85 | 6.31 |
|  | 1.0 | 6.80 | 7.92 | 6.85 | 6.38 |
|  | 0.5 | 6.80 | 7.69 | 6.85 | 6.32 |
|  | 0.1 | 6.80 | 9.03 | 6.85 | 8.78 |
| Dodecyl-pyridinium Chloride | 2.0 | 6.80 | 7.63 | 6.85 | 6.20 |
|  | 1.0 | 6.80 | 7.81 | 6.85 | 6.19 |
|  | 0.5 | 6.81 | 8.04 | 6.81 | 6.39 |
|  | 0.1 | 6.81 | 9.17 | 6.81 | 9.03 |
| Tetradecyl-Pyridinium Chloride | 2.0 | 6.80 | 7.79 | 6.82 | 6.15 |
|  | 1.0 | 6.80 | 7.81 | 6.82 | 6.14 |
|  | 0.5 | 6.80 | 7.63 | 6.82 | 6.19 |
|  | 0.1 | 6.80 | 9.04 | 6.82 | 8.96 |
| Cetyl-pyridinium Chloride | 2.0 | 6.80 | 7.74 | 6.82 | 6.18 |
|  | 1.0 | 6.80 | 7.57 | 6.82 | 6.39 |
|  | 0.5 | 6.80 | 8.04 | 6.82 | 6.54 |
|  | 0.1 | 6.81 | 9.06 | 6.82 | 8.92 |
| Tetradecyl-4-Ethyl Pyridinium Chloride | 2.0 | 6.80 | 7.77 | 6.82 | 6.15 |
|  | 1.0 | 6.81 | 7.94 | 6.81 | 6.36 |
|  | 0.5 | 6.80 | 7.92 | 6.82 | 6.22 |
|  | 0.1 | 6.80 | 9.10 | 6.82 | 9.09 |
| Methyl-Benzethonium Chloride | 2.0 | 6.80 | 8.19 | 6.82 | LOST |
|  | 1.0 | 6.80 | 9.24 | 6.82 | 6.64 |
|  | 0.5 | 6.80 | 9.12 | 6.82 | 8.53 |
|  | 0.1 | 6.80 | 9.26 | 6.82 | 9.01 |
| Benzalkonium Chloride | 2.0 | 6.80 | 7.91 | 6.76 | 6.19 |
|  | 1.0 | 6.80 | 8.06 | 6.76 | 6.52 |
|  | 0.5 | 6.80 | 7.85 | 6.76 | 6.68 |
|  | 0.1 | 6.80 | 9.11 | 6.76 | 8.94 |
| $CuSO_4$ | 5.0 | 6.81 | 8.19 | 6.81 | 6.35 |
|  | 2.0 | 6.81 | 8.90 | 6.81 | 6.85 |
|  | 1.0 | 6.81 | 9.08 | 6.81 | 6.35 |
|  | 0.5 | 6.81 | 9.10 | 6.81 | 8.53 |
| $ZnSO_4$ | 1.0 | 6.80 | 9.19 | 6.76 | 9.06 |
|  | 0.5 | 6.80 | 9.25 | 6.76 | 8.72 |
|  | 0.2 | 6.80 | 9.29 | 6.76 | 8.58 |
|  | 0.1 | 6.80 | 9.41 | 6.76 | 9.17 |
| Dodecyl-Trimethyl Ammonium Bromide | 10.0 | 6.80 | 7.84 | 6.79 | 6.29 |
|  | 5.0 | 6.80 | 7.82 | 6.79 | 6.24 |
|  | 2.0 | 6.80 | 7.86 | 6.79 | 6.39 |
|  | 1.0 | 6.80 | 7.73 | 6.79 | 6.39 |
| Tetradecyl Trimethyl Ammonium Bromide | 10.0 | 6.80 | 7.87 | 6.79 | 6.28 |
|  | 5.0 | 6.80 | 7.98 | 6.79 | 6.27 |
|  | 2.0 | 6.80 | 7.94 | 6.79 | 6.26 |
|  | 1.0 | 6.80 | 7.92 | 6.79 | 6.45 |
| Hexadecyl Trimethyl Ammonium Bromide | 10.0 | 6.80 | 7.83 | 6.86 | 6.30 |
|  | 5.0 | 6.80 | 7.64 | 6.86 | 6.42 |
|  | 2.0 | 6.80 | 8.04 | 6.79 | 6.26 |
|  | 1.0 | 6.80 | 8.05 | 6.79 | 8.37 |
| IRGASAN DP-300* | 0.4 | 6.80 | 8.00 | 6.86 | 6.34 |
|  | 0.2 | 6.80 | 8.03 | 6.86 | 6.44 |
|  | 0.2 | 6.80 | 8.13 | 6.86 | 6.38 |
|  | 0.05 | 6.80 | 8.12 | 6.86 | 6.40 |
| Lanthanum LAS | 10.0 | 6.80 | 8.13 | 6.86 | 6.27 |
|  | 5.0 | 6.80 | 8.12 | 6.86 | 6.34 |
|  | 1.0 | 6.80 | 7.64 | 6.86 | 6.40 |
|  | 0.5 | 6.80 | 7.87 | 6.86 | 7.94 |
| Phenol | 10.0 | 6.80 | 9.25 | 6.83 | 8.93 |
|  | 5.0 | 6.80 | 9.14 | 6.83 | 8.85 |
| Resorcinol | 10.0 | 6.80 | 9.12 | 6.83 | 9.10 |
|  | 5.0 | 6.80 | 9.11 | 6.83 | 9.31 |

*5-chloro-2-(2,4-dichlorophenoxy)phenol

The Table I data indicate that various combinations of antimicrobial agent and acidic buffer in the form of partially neutralized, polymeric gelling agent are effective in maintaining the pH of *Proteus vulgaris*-contaminated, bicarbonate-rich urine in the generally acid range, provided such combinations are used above a particular minimum concentration. In the absence of one component or the other in these pH control systems, pH of the urine does rise well into the alkaline range after 24 hours.

The Table I data further indicate that some conventional antimicrobial agents, even when used with the gelling agent buffer and at relatively high concentrations, are not effective in maintaining the requisite generally acidic pH of the *Proteus vulgaris*-contaminated, bicarbonate-containing urine. These relatively ineffective antimicrobial agents are thus not contemplated for use in the pH control systems of the absorbent articles herein.

EXAMPLE IV

A disposable diaper is prepared according to the teachings of U.S. Reissue Pat. No. 26,151. Such a diaper consists of a thin backsheet of polyethylene attached to a pad of absorbent airfelt formed by disintegrating drylap impregnated with 1% by weight of cetylpyridinium chloride (CPC). Impregnated drylap of this type is prepared in the manner described in Example I.

The combined backsheet and CPC airfelt wadding is overlaid with a compliant, porous, hydrophobic, nonwoven fabric web diaper liner (topsheet) having a weight of approximately 17 grams per square yard (20.3 g/m$^2$). Such a topsheet comprises 2.0 denier rayon and contains 28 percent by weight of a thermoplastic binder. The combined laminated structure is approximately 15×18 inches (38.1×45.7 cm) and is folded into a box pleat configuration by means of a multiplicity of longitudinal folds.

A hot melt of adipic acid is prepared by heating adipic acid above 152° C. The molten adipic acid is applied to the absorbent airfelt wadding prior to its assemblage in the above diaper by metering the acid melt with a positive displacement pump and by spraying the acid melt, at a rate of 1 gram/diaper, onto the absorbent airfelt wadding using two fan-shaped spray nozzles, one directed to the front of the diaper and one directed to the center. The spray rate of each nozzle is adjusted to around 90 grams/minute under a positive pressure of about 10 to 20 psi (69 to 138 kPa).

The resulting disposable diaper is especially effective at maintaining pH of urine discharged into the diaper at a value below about 7.5. Diapers of substantively similar pH control effectiveness are provided when the molten adipic acid is applied to the topsheet, backsheet, airfelt, absorbent pad or onto a tissue insert by roller printing techniques well known in the art.

EXAMPLE V

A flexible substrate suitable for use as an antimicrobial agent-containing diaper insert is prepared by airlaying a web of cellulose fiber (airfelt) formed by disintegrating the CPC-impregnated drylap described in Example I. Such a web has dimensions of 10 inches (25.4 cm)×4.5 inches (11.4 cm)×0.20 inches (0.50 cm) and a density of about 0.1 g/cm$^3$.

The insert substrate thus contains about 99% by weight airfelt and 1% by weight of the cetyl pyridinium chloride antimicrobial agent. The finished insert is prepared by wrapping this substrate in polypropylene diaper topsheet material (8 mils) and melt-bonding the overwrap at the ends.

An absorbent article of the present invention is prepared by positioning this insert substrate on top of the topsheet of a conventional absorbent gelling agent-containing diaper (e.g., ULTRA PAMPERS) which utilizes an absorbent core comprising particles of polyacrylate absorbent gelling buffering agent material admixed with airfelt. In such a configuration the polyacrylate absorbent gelling agent buffer comprises about 1.2% by weight of the insert/diaper combination. Such an insert/diaper combination provides effective control of the pH of *Proteus vulgaris*-contaminated urine within the absorbent article.

What is claimed is:

1. A disposable absorbent article useful for absorbing urine and feces discharged by incontinent individuals and also useful for reducing or preventing diaper rash, said absorbent article comprising
    (A) a liquid impervious backing sheet;
    (B) a relatively hydrophobic, liquid pervious topsheet;
    (C) an absorbent core positioned between said backing sheet and said topsheet, said absorbent core comprising hydrophilic fiber material, and
    (D) a pH control system consisting essentially of
        (i) an acidic buffering agent which releases protons when contacted with aqueous liquids, said buffering agent being in the form of particles of a partially neutralized, slightly cross-linked polymeric gelling agent having a gel volume of at least about 20 grams of synthetic urine per gram of gelling agent buffer, said particles being combined with the hydrophilic fiber material of the absorbent core and present within said core in a concentration of from about 2% to 50% by weight of the core; and
        (ii) an antimicrobial agent selected from quaternary nitrogen-based compounds and bis-biguanide compounds, said antimicrobial agent being combined with said absorbent core and present in or on said core in a concentration of from about 0.02% to 2.0% by weight of the core;
said buffering agent compound and said antimicrobial agent component being present within said pH control system in a weight ratio of from about 3:1 to 2000:1 with said pH control system being present in said absorbent article in an amount which is effective to maintain the pH of *Proteus vulgaris*-contaminated, bicarbonate-containing urine discharged into said article at a value below about 7.5.

2. An article according to claim 1 wherein
    (A) the polymeric gelling agent buffer is selected from the group consisting of hydrolyzed acrylonitrile grafted starch, acrylic acid grafted starch, polyacrylates, maleic anhydride-based copolymers and combinations of these polymeric gelling agent buffers;
    (B) the antimicrobial agent is selected from the group consisting of methylbenzethonium chloride, benzalkonium chloride, dodecyltrimethyl ammonium bromide, tetradecyltrimethyl ammonium bromide, hexadecyltrimethyl ammonium bromide, dodecylpyridinium chloride, tetradecylpyridinium chloride, cetylpyridinium chloride, tetradecyl-4-ethylpyridinium chloride, tetradecyl-4methylpyridinium chloride, chlorhexidine, the water-soluble salts of chlorhexidine and combinations of these antimicrobial agents; and (C) the weight ratio of the acidic buffering agent component to the antimicrobial agent component ranges from about 25:1 to 1000:1.

3. A disposable absorbent article in the form of a diaper or incontinence brief, said article comprising
(A) a liquid impervious polyolefin backing sheet;
(B) a relatively hydrophobic, liquid pervious topsheet formed from polyester or polyolefin fibers or film;
(C) an absorbent core positioned between said backing sheet and said topsheet, said absorbent core comprising hydrophilic fiber material, and
(D) a pH control system consisting essentially of
 (i) an acidic buffering agent which releases protons when contacted with aqueous liquids, said buffering agent being in the form of particles of a partially neutralized, slightly cross-linked sodium polyacrylate polymeric gelling agent having a gel volume of from about 30 to 60 grams of synthetic urine per gram of gelling agent buffer, said particles being combined with the hydrophilic fiber material of the absorbent core and present within said core in a concentration of from about 5% to 20% by weight of the core; and
 (ii) an antimicrobial agent selected from cetylpyridinium chloride and the water-soluble salts of chlorhexidine; said acidic buffering agent and said antimicrobial agent component being present within said pH control system in a weight ratio of from about 25:1 to 1000:1.

4. A diaper or incontinence brief according to claim 3 wherein
(A) said topsheet is coextensive with one face of said core;
(B) said backing sheet is coextensive with the face of the core opposite the face covered by said topsheet;
(C) both said topsheet and said backing sheet have a width greater than that of the core, to thereby provide side marginal portions of the topsheet and backing sheet which extend beyond the core; and
(D) said absorbent core is generally hourglass-shaped.

5. A diaper or incontinence brief according to claim 4 wherein the absorbent core comprises an airlaid web of hydrophilic fibers and the particles of the polymeric gelling agent buffer, said web having a density of from about 0.06 to 0.3 g/cm$^3$.

6. A diaper or incontinence brief according to claim 5 wherein the hydrophilic fibers of the absorbent core are wood pulp fibers.

7. A diaper or incontinence brief according to claim 6 wherein said antimicrobial agent is impregnated into the hydrophilic fibers forming the absorbent core and comprises from about 0.05 to 1.0% by weight of said core.

8. A diaper or incontinence brief according to claim 6 wherein said antimicrobial agent is intimately associated with said topsheet.

9. A diaper or incontinence brief according to claim 6 wherein said antimicrobial agent is incorporated in or on a water-insoluble, flexible substrate positioned as an insert on top of the topsheet of the diaper or incontinence brief such that, when the diaper or incontinence brief is worn, the insert is next to the wearer's skin.

10. A diaper or incontinence brief according to claim 9 wherein the flexible substrate insert comprises a material selected from cellulose fibers, polyolefins, polyesters and rayon.

11. An article according to claim 9 wherein the absorbent core comprises
(A) from about 60% to 95% by weight of hydrophilic fiber material selected from wood pulp fibers;
(B) from about 5% to 20% by weight of a partially neutralized, slightly crosslinked sodium polyacrylate polymeric gelling agent buffer; and
(C) from about 0.05 to 1.0% by weight of an antimicrobial agent selected from cetylpyridinium chloride and the water-soluble salts of chlorhexidine.

12. An article according to claim 11 wherein the polymerizing gelling agent buffer has a gel volume of from about 30 to 60 grams of synthetic urine per gram of gelling agent buffer and an equilibrium extractable polymer content in synthetic urine of no more than about 17% by weight.

13. An article according to claim 12 wherein the absorbent core comprises an airlaid web of hydrophilic fibers having incorporated therein both the antimicrobial agent and particles of the polymeric gelling agent buffer, said web having a density of from about 0.06 to 0.3 g/cm$^3$.

14. A diaper or incontinence brief according to claim 10 wherein said insert covers from about 20% to 90% of the topsheet surface area.

15. A diaper or incontinence brief according to claim 10 wherein said insert has thickness of from about 0.2 to 1.5 cm.

* * * * *